United States Patent
Gerl et al.

(10) Patent No.: US 7,169,562 B1
(45) Date of Patent: Jan. 30, 2007

(54) IMMUNOLOGIC ASSAY TO DETERMINE C-PEPTIDE CONTAINING IMPURITIES IN SAMPLES OF HUMAN INSULIN AND DERIVATIVES THEREOF

(75) Inventors: Martin Gerl, Niedernhausen (DE); Cornelia Steinert, Wiesbaden (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 838 days.

(21) Appl. No.: 09/695,919

(22) Filed: Oct. 26, 2000

(30) Foreign Application Priority Data

Oct. 27, 1999  (DE) ................... 199 51 684

(51) Int. Cl.
*G01N 33/53* (2006.01)
(52) U.S. Cl. ............... 435/7.1; 435/7.93; 435/7.94; 435/7.95; 436/15; 436/86
(58) Field of Classification Search ............ 435/6, 435/7.1, 7.93, 7.95, 69.7, 69.1; 436/15, 86
See application file for complete search history.

(56) References Cited

U.S. PATENT DOCUMENTS 5,811,266 A * 9/1998 Newgard ............... 435/69.4
6,444,641 B1 * 9/2002 Flora ..................... 514/3
6,635,745 B2 * 10/2003 Sedrani et al. ........... 530/405

FOREIGN PATENT DOCUMENTS

EP    0 484 961 A1    5/1992

OTHER PUBLICATIONS

Campbell Alice section 1.3.4. p. 29; Monoclonal Antibody Technology (1984) Elsevier Science Publishers).*
Naithani et al. Syntheses of monkey C-peptide derivatives Fed. Rep. Ger. International Congress Series (1979) 468: 94-98.*
Iizuka et al. An Improved method for determination of human C-peptide in serum and urine. Biomedical Research (1990) 11: 417-423.*
International Search Report to PCT/EP 00 10482 (May 7, 2001).
Derwent Abstract—WO 98/59246, abstract only.
V.K. Naithani & L.G. Heding, "Synthesis of Monkey C-Peptide Derivatives," *Proceedings of the Symposium on Proinsulin, Insulin, and C-Pepetide*, Tokushima, Japan, Jul. 12-14, 1978, S. Baba et al., Eds., Exerpta Medica, Amsterdam-Oxford, pp. 94-98 (1979).

* cited by examiner

*Primary Examiner*—Long V. Le
*Assistant Examiner*—Jacob Cheu
(74) *Attorney, Agent, or Firm*—Mark C. Nelligan

(57) ABSTRACT

The invention relates to a process for detecting or determining a C-peptide-containing impurity in a sample of recombinantly produced human insulin or a derivative thereof, by a non-radioactive assay, comprising the steps:
(a) preparing a sample of recombinantly produced human insulin or a derivative thereof;
(b) mixing the samples with dilution buffer;
(c) adding a tracer to mixture (b);
(d) adding antibody specific for the C-peptide impurity to mixture (c);
(e) adding "C-peptide second antibody bead" having at least one label to mixture (d); and
(f) detecting or determining the presence of the C-peptide-containing impurity.

12 Claims, 8 Drawing Sheets

EXPLANATIONS

= A-CHAIN OF INSULIN

= B-CHAIN OF INSULIN

= C-PEPTIDE

= PRESEQUENCE OF RECOMBINANT INSULINS

= COVALENT BOND BETWEEN "SH" OF CYSTEINES

ADC1 A, SIGNAL FROM PC LOOP (5\SDPE_008.D)

ADC1 A, SIGNAL FROM PC LOOP (5\SDPE_031.D)

IMMUNOLOGIC ASSAY TO DETERMINE C-PEPTIDE CONTAINING IMPURITIES IN SAMPLES OF HUMAN INSULIN AND DERIVATIVES THEREOF

Recombinant insulins are produced by down-stream processing of fusion proteins expressed by transformed *E. coli*. After the folding reaction, insulin precursors containing the correct disulfide bridges of insulin are cleaved out of the preproinsulin by treatment with trypsin, which liberates the C-peptide by synchronous cleavage at the sequence positions -Arg-Arg-(B31-B32) and -Lys-Arg-(A1-A0). The amino acid sequence of the monkey C-peptide differs from the human C-peptide by only one amino acid at position 37 (Pro vs. Leu).

After the purification process, the final product, human insulin, must be analyzed for the presence of minute amounts of preproinsulin and its derivatives, C-peptide containing insulin derivatives, and isolated C-peptide (collectively denoted as C-peptide-like activity). In the following, the abbreviations "HI" is used for "human insulin", "HIA1" is used for "Gly(A21)-Arg(B31)-Arg(B32)-human insulin", and "HIA2" is used for "Lys(B3),Glu(B29)-human insulin", respectively. This analysis is usually performed by radioimmunoassay ("RIA").

The disadvantage of the RIA method is that it requires a freshly iodinated tracer and a 3-day incubation period with all the connected unfavorable logistics. In addition, sample preparation is very time consuming, sensitive to changes, and previous measurements have shown that the assay, in some cases, is not free from unpredictable interference from tracer quality, sample handling, and precipitation during the 3-day incubation. The consequence is wasted time due to the need for repetitions. An additional drawback of the RIA method is that it cannot be applied on HIA1 or HI samples from purification steps before carboxypeptidase B ("CPB") cleavage because these samples precipitate at the given pH of the assay method. Increasing the pH of the RIA assay buffer improves sample dissolution, but decreases the assay performance. The object of the present invention was to produce antibodies that can be applied in an immunoassay to quantify insulin C-peptide containing impurities in a final pure insulin preparation obtained in a specific purification batch ("end probes") of HI (INSUMAN™), HIA1 (GLARGINE™), and HIA2 production, as well as in in-process batch step samples of the three insulin variants.

The antibodies should show affinity to isolated monkey C-peptide and preproinsulin ("PPI"), but they also should be able to bind to model compounds, such as PPI, human and/or monkey C-peptide, HI reduced/alkylated, HI cleaved with endoproteinase Asp-N at the EDP, HIA2 C-peptide, and HIA2 PPI, which are designed to reflect a panel of putative side products and impurities that can be anticipated in the industrial recombinant production of insulin.

An antibody preparation fulfilling the requirements described above can be used in a suitable assay format to quantify insulin C-peptide-like immunoreactivity in end probes of insulin purification, as well as in selected in-process batch step samples.

Due to the physical properties of the test batch step samples, the antibodies used must interact with the antigens with sufficient affinity at a pH of about 8.5–9.0. The interaction must not be influenced by the sample matrix, which is characterized by an insulin content of about 1 mg/mL. The immunoassay must be able to quantify C-peptide containing impurities (insulin C-peptide-like immunoreactivity) below 10 ng/mL (10 ppm compared to human insulin).

In theory, several C-peptide containing impurities can be expected as side products of insulin production. They are shown in FIG. 1A.

SUMMARY OF THE INVENTION

A process for detecting or determining a C-peptide impurity in a sample of recombinantly produced human insulin or a derivative thereof, by a non-radioactive assay, comprising the steps:
   (a) preparing a sample of recombinantly produced human insulin or a derivative thereof;
   (b) mixing the samples with dilution buffer;
   (c) adding a tracer to mixture (b);
   (d) adding antibody to mixture (c);
   (e) adding "C-peptide second antibody bead" having at least one label to mixture (d); and
   (f) detecting or determining the presence of a C-peptide impurity.

BRIEF DESCRIPTION OF THE FIGURES

FIG. 1 B provides an explanation of symbols in FIG. 1A.

FIG. 4 B depicts the elution profile of an isolated serum sample containing anti-monkey insulin C-peptide antibodies applied to a PPI EMD Azlacton column.

DESCRIPTION OF THE INVENTION

Figure 1A:
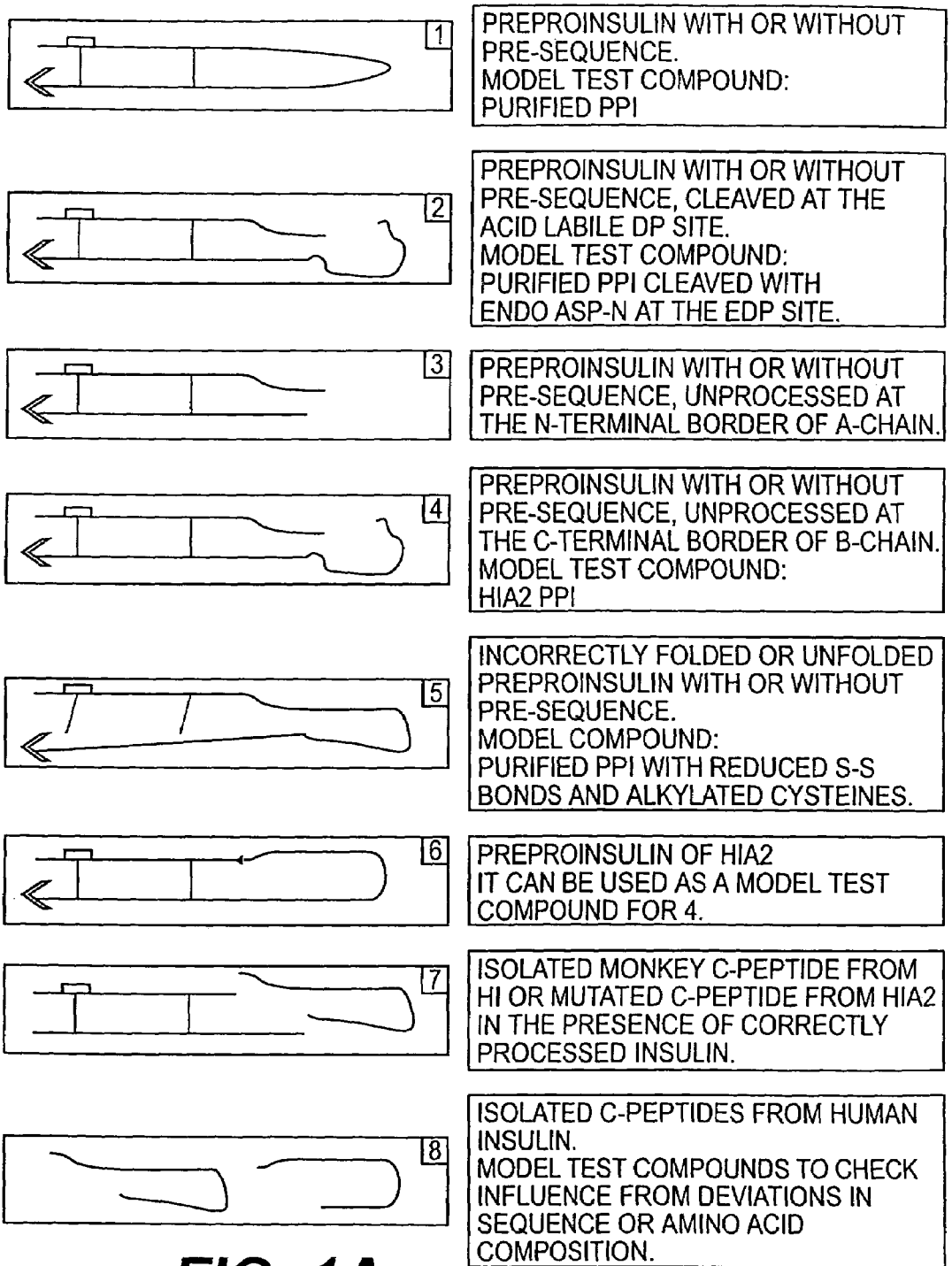
FIG. 1 A diagrams putative C-peptide containing impurities.
Figure 1B:
Figure 1B:
Figure 1B:
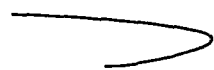
Figure 1B:
Figure 1B:

The present application describes a new non-radioactive immunoassay circumventing the above-described disadvantages of the original RIA. The new assay is based on:

1. Antibodies from sheep S95-11 affinity purified on PPI.
2. A simplified two-step sample dilution procedure without pH control and pH adjustment after sample dissolution in each sample.
3. A chemiluminescent C-peptide tracer, which is stable for a long time, so that the assay can be performed with the identical tracer over a long period of time.
4. Polystyrol beads coated with secondary antibodies (Daiichi Radioisotope Labs. LTD) to capture goat antiinsulin C-peptide antibodies with or without bound antigens or tracer.
5. A one step simultaneous incubation of all components of only 5 hours duration.

Since the assay is performed at a pH=8.5–8.7, both HI and HIA1 test batch step samples remain dissolved during the whole incubation period and can be analyzed using the same assay without any variation.

Since the C-peptide of recombinant insulin HI and HIA1 is taken from monkey proinsulin, an assay suitable to detect monkey insulin C-peptide is needed to quantify insulin C-peptide-like immunoreactivity in HMR recombinant insulin end probes and in-process batch step samples.

The C-peptide of HIA2 is mutated and truncated at the C-terminal region when compared to the C-peptide of human insulin, hence it is artificial and not a naturally occurring peptide.

There are some diagnostic immunoassays available commercially that can be applied to determine the concentration of insulin C-peptide in serum. All assays show species specificity to human insulin C-peptide, some to rat, bovine, and porcine, but none to monkey C-peptide.

The purpose of the commercially available assays is to make them as specific as possible for either C-peptide or proinsulin. Our intention, however, was to obtain antibodies (an assay) that interact with both C-peptide and PPI with nearly the same affinity.

The antibodies used in the process of the present invention are obtained by immunizing a mammal, preferably a sheep, with the purified C-peptide of insulin, preferably the C-peptide of monkey insulin as described in European patent 0 032 675, followed by affinity purification with insulin immobilized on a suitable carrier, wherein the insulin preferably is semisynthetic human insulin or recombinant human PPI. The purification of the antibodies is described in the examples and attachments.

We tested three commercially available assays to determine whether they fulfill the needed requirements. The three assays were (1) RIA-coat C-peptide; (2) Human C-peptide RIA Kit; and (3) Human Proinsulin RIA Kit.

1. RIA-Coat C-Peptide (Cat. # 323.171 from BYK Sangtec Diagnostica GmbH & Co. KG 63120 Dietzenbach, Germany; 3-Hour Protocol)

This assay was not suitable to quantify monkey insulin C-peptide in the given samples. This may be due to:
 a) An insufficient cross reactivity with monkey C-peptide and/or PPI (25% according to supplier);
 b) Inappropriate constituents of sample buffer; or
 c) Disturbance by the high concentrations (1 mg/mL) of human insulin in the samples.

2. Human C-Peptide RIA Kit (Cat.# HCP-20 K from Linco Research Inc. St. Louis, Mo. 63304-USA, 2-Day Assay Protocol)

This assay is based on antibodies against human C-peptide that show a 90% cross-reactivity to monkey C-peptide and <4% crossreactivity to human proinsulin.

The Linco assay can be applied to analyze the given HI samples. However, due to the pH of the kit buffers, precipitation of in-process batch step samples of HI production occurs. In the case of HIA1, which is not soluble at pH 7.4, the assay cannot be applied. A comparison with the chemiluminescent coated bead assay of the present invention shows that although the antibodies used in the assay are more potent in binding to isolated C-peptide from human and monkey origin, they do not interact as well with HI, PPI, or PPI cleaved at the EDP site as the antibody preparation of this invention. It should be noted that the coated bead assay of the present invention is performed at pH 8.7, whereas the Linco assay is performed at pH 7.4.

3. Human Proinsulin RIA Kit, Cat.# HPI-15K, K from Linco Research Inc. St. Louis, Mo. 63304-USA (3-Day Assay Protocol)

This assay is not able to detect monkey C-peptide, thus its specificity is not sufficient for our needs.

In conclusion, our requirements cannot be fulfilled by assays based on antibodies against human C-peptide or human proinsulin that are performed at neutral pH.

Requirements for the Assay are:
 Assay pH >8.5;
 Sufficient specificity for PPI;
 Sufficient binding affinity for the model test compounds;
 The presence of 1 mg/mL HI does not interfere with the binding affinity of the antibody;
 No radioactivity; and
 Short assay times.

Strategy to Obtain the Assay Needed:
 Immunization with monkey insulin C-peptide not coupled to a carrier;
 Affinity purification with a PPI column;
 Eliminate by immunoadsorption any antibodies that specifically or non-specifically interact with human insulin
 Screen antibodies from different bleedings by investigating their binding to chemiluminescent C-peptide tracer at pH 8.5;
 Generate model test compounds; and
 Establish an assay at pH >8.5 using a buffer with high buffer capacity at that pH.

The invention will be described now by the examples, without being limited thereto.

EXAMPLES

In the following examples, some or all of the following materials and equipment were used:

Double-distilled Water

Monosodium phosphate, Riedel (04269)

Sodium Chloride, Merck

Sodium azide, Merck

Serum albumin bovine, Behringwerke (ORHD 20/21)

Gamma globulin bovine, Sigma (G-5009)

Glycine, Riedel (33226)

Polyethylene Glycol-20% ("PEG-20"), Biodata

Sodium hydroxide-Fixanal, Riedel (38210)

Sodium hydroxide-2M, Riedel (35254)

Sodium acetate trihydrate, Merck (6267)

Phosphoric acid, 85%, Riedel (30417)

Semisynthetic human insulin (HIet), Batch: A48 U114 and A48 U118

RIA Polystyrene tubes, 12×75 mm, Sarstedt (55476)

C-peptide second antibody beads, CPIII, Daiichi Radioisotope Labs; LTD, Tokyo

Proclin 300, Supelco Inc. (Bellafonte, Pa.) (4-8127)—a preservative for diagnostic reagents.

Dulbecco's Phosphate Buffered Saline ("PBS"), Sigma (D-5652)

Berilux solutions R1 and R2, Behringwerke (OCNH 02/03)—preformed analyzer reagents used to initiate chemiluminescence with acridinium labels. Solution R1 is composed of 0.5% $H_2O_2$ and 0.1M $HNO_3$. Solution R2 is composed of a dilute solution of NaOH.

Sensor chips CM5, Pharmacia BIACORE®

Carbodiimide coupling kit, Pharmacia BIACORE®

BCA assay to quantitate protein concentration, Pierce (solution A: No.23223; solution B: 23224)

IgG Standard for determination of protein concentration, Pierce (31204)

Fractogel EMD Azlacton 650 (S), Merck (1.10087)

SDS Gel electrophoresis system using NuPAGE 4–12% and MES running buffer, Novex Silver Staining Kit Plus One, Pharmacia Biotech (Code # 17-1150-01)(All other Chemicals were purchased from Sigma, Merck, or Riedel de Haen.)

Equipment:
Multipette, Eppendorf
Microliter pipettes, Abimed, Gilson
Microlab M, Hamilton
Measuring flasks and graduated cylinders
Whirlymixer Reax 2000, Heidolph
Digital-pH-Meter, Knick
AutoCliniLumat LB 952 T/16, Berthold
Wallac Wizard 1470 multidetector gamma counter (with RIA-Calc, Multi-Calc software), Wallac
BIACORE® 1000, Pharmacia BIACORE®
Cool centrifuge (GS-6), Beckmann
Suprafuge 22, Heraeus Sepatech
Biogfuge 13 R, Megafuge 1.0 R, Heraeus Sepatech
SDS Gel electrophoresis System including power supplies Model 3540, Novex
Eppendorf tube incubator, Eppendorf
Hoefer automated gel stainer, Pharmacia
Balances PM400, PM4000, Mettler
AT261 Delta Range, Mettler
Ultrafree-15 10 kDa, Millipore (UFV2BGC)
Glass prefilter Ø 47 mm, Schleicher & Schüll (421026)
Membrane filter Ø 50 mm, 5 µm, Schleicher & Schüll (400214)
Membrane filter Ø 50 mm, 0.2 µm, Schleicher Schüll (404114)

FPLC 1 (Pharmacia) for Affinity Chromatography:
Controller LCC-500 Plus
2×Pump P-500
Pump P50
Pump P-1
Uvicord SII and conductivity detectors
ERC 3312 Degasser
2211 Superrac fraction collector
4×MV-8 valves
1×MV-7 valve FPLC 2 (Pharmacia) for Gel Permeation Chromatography:
Controller LCC-500 Plus
2×Pump P-500
Pump P-1
Uvicord S detector
ERC 3612 Degasser
2211 Superrac fraction collector
1×MV-7 valve
Flow stopper
Manual valve SRV-4

Abbreviations:
BSA: bovine serum albumin
CV: coefficient of variation
ELISA: enzyme linked immunosorbent assay
HIet: semisynthetic human insulin
PBS: phosphate buffered saline
PPI: preproinsulin
QC: quality control
RIA: radioimmunoassay Specific Assay Ingredients Used in the Following Examples:

Antibodies:

The antibodies were obtained by immunizing a sheep (S95-11) with purified insulin C-peptide. The serum sample obtained by bleeding the animal was purified according to the purification protocol in Example 1. The resulting affinity purified antibodies can be used in the present assay at a dilution of 1:1500.

The following antibodies were obtained:
Z2127, 99Ser1_SD2/F17-22
Z94, 99Ser2_SD2/P3
S95-11, 99Ser7/SD2-650/F17-22
S95-11, 99Ser8/SD2-651/F17-21
S95-11, 99Ser9/SD2-652/F17-24
S95-11, 99Ser10/SD2-680/F15-25
S95-11, 99Ser11/SD2-681/F15-24
S95-11, 99Ser12/SD2-682/F15-24

Tracer and Standard Material:

Isolated C-peptide (monkey instead of human sequence) from recombinant human HI insulin is used as standard and tracer. The purity is 99%.

Sample Buffer:

The sample buffer is prepared by dissolving 0.326 g Bicine (Sigma B-3876) in 100 mL distilled $H_2O$. The pH is adjusted to 8.7 using 1N NaOH.

Standard/Dilution Buffer:

Semisynthetic human insulin (Hlet, see Materials) is dissolved in 10 mM HCl resulting in a 10 mg/mL solution. This insulin solution is further diluted 1:10 using sample buffer.

Antibody Buffer:

The commercially available PBS powder (Sigma D-5652) is dissolved in about 980 mL of water, the pH is adjusted to 7.7 by adding 1N NaOH. TWEEN-20® is added to yield a 0.05% final concentration of this detergent. The volume of the buffer is adjusted to exactly 1 L in a graduated cylinder. Finally, BSA is dissolved to yield 1.5% (w/v).

DETAILED EXAMPLES

Example 1

I. Assay Performance

A. Sample Dissolution:

About 0.5–0.8 mg of the sample was dissolved in 10 mM HCl to result in a 10 mg/mL solution. Subsequently, the completely dissolved material was further diluted 1:10 using sample buffer.

B. Tracer Preparation:

By using the acridiniumacylsulfonamide derivative Ki 256 (German patents DE 3805318 and DE 3628573, respectively), a C-peptide tracer can be produced by its direct covalent conjugation with a luminescent acridinium ester moiety. Chemiluminescence can be induced by addition of alkaline $H_2O_2$ (McCarpa, F. (1976) Acc. Chem. Res. 9: 201 ff.).

To prepare this chemiluminescent C-peptide tracer the following solutions were mixed and incubated for 20 minutes at ambient temperature:

1. 255 µl of a buffer containing 8.17 g $KH_2PO_4$, 7.12 g $Na_2HPO_4$, 8.77 g NaCl, and 0.5 g $NaN_3$ in 1 L $H_2O$. The pH was adjusted to 8.0 using 1N NaOH.
2. 125 µl of C-peptide at a concentration of 2 mg/mL in $H_2O$,
3. 120 µl of label Ki 256 (10 mg in 1 mL acetonitrile).

The covalent reaction of the label with functional groups in the C-peptide was stopped by addition of 100 µl of L-lysine (10 mg/mL). The labeled C-peptide was purified by size exclusion gel-chromatography using a Superdex Peptide 10/30 column (Pharmacia) integrated in a FPLC system. The running buffer was PBS, 0.04% Proclin. Flow rate was 0.2 mL/min.

The protein eluted at the position between aprotinin and cytochrome C was collected, pooled, and frozen in aliquots (Batch 2). Reproducibility of tracer production has been proved once. The optimal dilution of the tracer stock solution for application in the assay was determined empirically.

Figure 2:
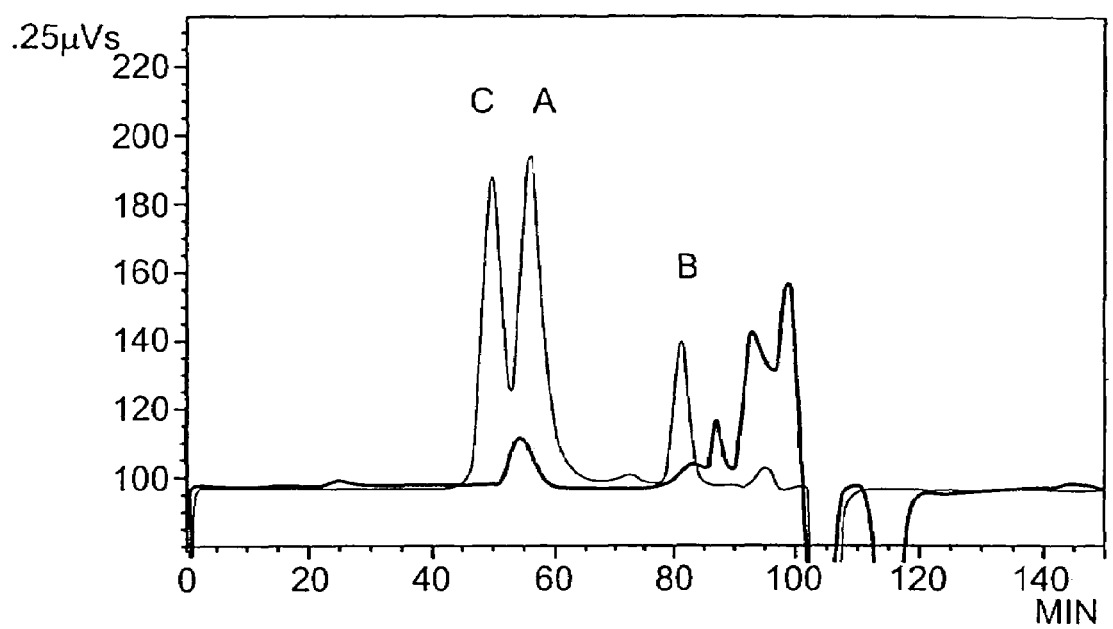
FIG. 2 depicts the elution profile for calibrators cytochrome C(C), aprotinin (A), and vitamin B1 (B) with Superdex peptide (10/30). The C-peptide tracer elutes in a symmetrical peak at a position between cytochrome C and aprotinin (bold line).

C. Tracer Purification with Superdex-Peptide (10/30):

The elution of calibrators, cytochrome C(C), aprotinin (A), and vitamin B1 (B) are depicted in FIG. 2. Unreacted label, lysine, and other buffer components can be eliminated from the tracer that elutes in a symmetrical peak at a position between cytochrome C and aprotinin (bold line).

D. Standard Preparation:

A 1 mg/mL stock solution of insulin C-peptide (according to # 2 below) in water is prepared. From this stock an aliquot is taken and further diluted 1:100 in dilution buffer. Both samples are stored frozen until use.

The standards are prepared from the latter (10 µg/mL) sample by diluting an aliquot with dilution buffer 1:100 and subsequently 4-times by 1:4 resulting in standards of 100 ng/mL, 25 ng/mL (S4), 6.25 ng/mL (S3), 1.563 ng/mL (S2) and 0.39 ng/mL (S1). All dilutions are performed in dilution buffer containing 1 mg/mL Hlet in order to mimic the conditions in unknown insulin samples from production. Only standards S1–S4 are used in the assay.

II. Assay Protocol

1. Standards are prepared in triplicates using 200 µl of each standard concentration per tube.
2. Samples are analyzed in duplicates using 200 µl of dissolved samples.
3. Pure dilution buffer is used (3×200 µl) to obtain S0—values.
4. The tracer (Batch 2) is diluted 1:40,000 in sample buffer. 100 µl of this tracer solution is added to each tube.
5. Antibody preparation 99Ser9 is diluted 1:1500 in antibody buffer and 100 µl is added to each tube.
6. The contents in the tubes are mixed. Afterwards one "C-peptide second antibody bead", is added.
7. After 5 hours shaking at ambient temperature, the liquid is withdrawn by suction. The beads are washed 5 times with about 0.8 mL water using a manual 10 tip wash head connected to a vacuum pump. Subsequently, the samples are analyzed in the luminometer. Chemiluminescence in the sample is stimulated by automated successive dispersion of 0.3 mL solution R1 ($H_2O_2$) and R2 (NaOH), each. The emitting light is measured for 1 second and displayed as RLU (relative light units).
8. Calculation of the results is performed automatically by the software based on the analyzer itself using a logit/log transformation of the standard curve.

III. Assay Characteristics

Variation Around the Real Background

A. Determination of Semisynthetic Human Insulin

The purpose of the assay is to identify PPI, insulin C-peptide, and putative insulin impurities that contain parts of the C-peptide covalently linked to the A- or B-chain of human insulin. These antigenic structures have to be determined in the presence of an excess of correctly processed insulin. To analyze the variation induced by this insulin background, semi-synthetic insulin (at concentrations of 1 mg/mL) was analyzed repeatedly. Semi-synthetic insulin must be used for this purpose to ensure that it does not contain impurities from monkey C-peptide, and in addition, it is a component of the standard/dilution buffer.

Semi-synthetic insulin was dissolved 10 fold at a concentration of 1 mg/mL as described in sample dissolution above. These insulin samples were analyzed in the assay on the same day. The results obtained with the insulin samples are shown in Table 1.

TABLE 1

Results obtained in samples of 1 mg/mL semi-synthetic Human insulin and insulin HIA1 from step 12/10 of the purification process

| Sample description<br>Sample number | Hlet<br>B/B0 (%) * | HIA1 055AKR<br>01 + 02<br>B/B0 (%) * |
|---|---|---|
| 1 | 91.5 | 80.0 |
| 2 | 105.1 | 79.8 |
| 3 | 101.8 | 85.9 |
| 4 | 102.6 | 86.7 |
| 5 | 105.6 | 77.7 |
| 6 | 91.3 | 82.2 |
| 7 | 102.1 | 85.0 |
| 8 | 106.3 | 84.1 |
| 9 | 103.1 | 80.0 |

TABLE 1-continued

Results obtained in samples of 1 mg/mL semi-synthetic Human insulin and insulin HIA1 from step 12/10 of the purification process

| Sample description Sample number | HIet B/B0 (%) * | HIA1 055AKR 01 + 02 B/B0 (%) * |
|---|---|---|
| 10 | 101.0 | 77.2 |
| mean value | 101 | 81.9 |
| standard deviation | 3.9 | 3.4 |

* all samples were determined in duplicate.

B0 represents the maximum response possible between the antibody and the tracer (without inhibitor) in a given test system (100% binding). B/B0 is the ratio of the signal obtained for a sample (standard or unknown) to B0. The results show that semisynthetic human insulin, on average, does not perturb binding of the tracer to the antibody. However, there is a certain variability resulting in maximal values of B/B0 of 106% and minimal values of 91%.

The consequence of this finding is that values above B/B0 of 90% (=mean value minus 3-times the standard deviation) obtained in unknown samples should not be calculated and was interpreted as background (detection limit). A sample yielding B/B0>90% most probably contains <0.4 ppm C-peptide-like activity. Repeatability (intra assay variability), as analyzed with these HIet (background) samples, is 4%.

The same value of 4% was found in a sample that contains about 1 ng/mL C-peptide-like immunoreactivity (sample HIA1 055 AKR 01+02, see Table 1). Like the HIet probe, the test batch step sample was dissolved 10-times at a concentration of 1 mg/mL and analyzed on the same day.

B. Applying the Statistical Approach on Insulin End Product Samples

The same statistical approach has been applied on end products of HI and HIA1 production. For this purpose, 23 different samples of HI and 6 different samples of HIA1 were analyzed on the same day. The results are shown in Table 2.

TABLE 2

Results obtained in samples of 1 mg/mL HI and HIA1

| HI | | HIA1 | |
|---|---|---|---|
| Sample code | B/B0 (%) * | Sample code | B/B0 (%) * |
| C038 | 99.3 | U012 | 88.91 |
| U030 | 93.2 | U018 | 90.99 |
| C033 | 92.5 | U019 | 88.33 |
| C034 | 89.8 | U020 | 76.91 |
| C035 | 100.2 | U021 | 89.24 |
| C036 | 99.4 | U022 | 90.83 |
| C037 | 97.4 | | |
| C039 | 90.8 | | |
| C040 | 93.8 | | |
| C041 | 99.5 | | |
| C042 | 102.7 | | |
| C044 | 102.2 | | |
| C045 | 104.9 | | |
| C046 | 92.5 | | |
| C047 | 100.8 | | |
| C048 | 106.3 | | |
| C049 | 108.9 | | |
| C050 | 101.6 | | |
| C051 | 94.7 | | |
| C052 | 101.7 | | |
| C053 | 98.9 | | |

TABLE 2-continued

Results obtained in samples of 1 mg/mL HI and HIA1

| HI | | HIA1 | |
|---|---|---|---|
| Sample code | B/B0 (%) * | Sample code | B/B0 (%) * |
| C054 | 102.3 | | |
| C043 | 100.2 | | |
| mean value | 98.9 | | 87.53 |
| Standard deviation | 5.0 | | 3.54 |

* all samples were determined in duplicate.

The data clearly show that end products of HI on average contain no C-peptide-like activity because the variation around the single determinations is similar to that obtained with semisynthetic human insulin. There is no significant difference between the HI group (of 24 individual samples) and HIet (one sample analyzed 10 times in the same assay). The minimum and maximum values in the HI samples (89.8% or 109%, respectively) also are close to the values obtained with HIet (91% or 106%, respectively).

Regarding HIA1 samples, it can be concluded that C-peptide-like immunoreactivity is present in the end product. However, the content is in the range of 0.5–1 ppm (when quantitated with the help of a standard curve, see below).

Figure 3:
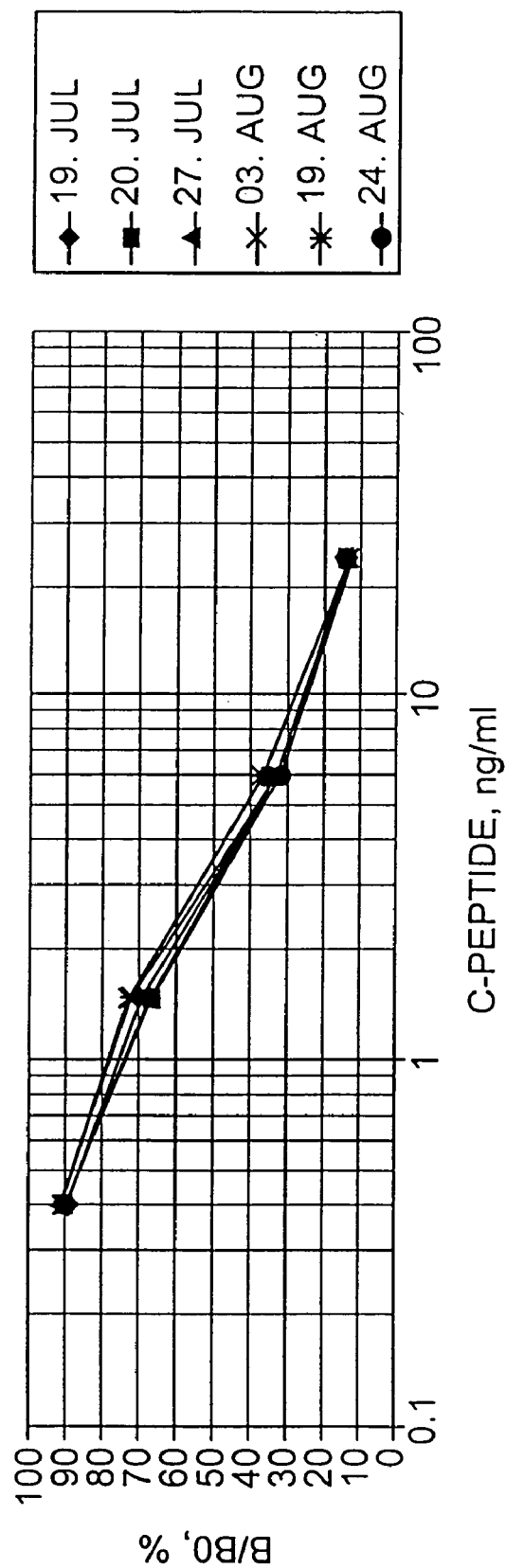
FIG. 3 depicts standard curves obtained in 6 different assay runs for detecting and identifying C-peptide impurities in semisynthetic human insulin preparations.

C. Standard Curve:

The standard curves obtained in 6 different assays are illustrated in FIG. 3. The numerical values of these curves expressed as B/B0 (%) are summarized in Table 3. The curve statistics are given in Table 4.

TABLE 3

Original data of the standard curves

| Standard ng/mL | Dates of assay performance | | | | | |
|---|---|---|---|---|---|---|
| | July 19 B/B0 | July 20 B/B0 | July 27 B/B0 | August 03 B/B0 | August 19 B/B0 | August 24 B/B0 |
| 0.39 | 89.2 | 92 | 93.6 | 93.6 | 92.5 | 91.0 |
| 1.56 | 68.4 | 66.6 | 67.9 | 71.2 | 71.8 | 68.8 |
| 6.25 | 32.4 | 32.5 | 35.7 | 34.6 | 35.8 | 35.9 |
| 25.0 | 13.5 | 13.8 | 14.3 | 14.5 | 14.1 | 13.8 |

The curve parameters are:

$ED_{20}=14.44\pm0.99$ ng/mL (CV=6.86%)

$ED_{50}=3.21\pm0.23$ ng/mL (CV=7.21%)

$ED_{80}=0.91\pm0.10$ ng/mL (CV=10.71%)

TABLE 4

Statistical evaluation of data obtained from 6 standard curves and control samples measured on different days:

| Standard (ng/mL) | mean value (B/B0) | Standard deviation (B/B0) | CV (%) |
|---|---|---|---|
| 0.39 | 92.0 | 1.69 | 1.83 |
| 1.56 | 69.1 | 2.0 | 2.89 |
| 6.25 | 34.4 | 1.61 | 4.68 |
| 25.0 | 14 | 0.37 | 2.63 |
| Control, HIet (5 determinations) | 97.80 | 3.82 | 3.90 |
| Control HI batch C038 (5 determinations) | 98.65 | 2.92 | 2.97 |

The above presented data show:
1. The standard curve is highly reproducible.
2. Semi-synthetic human insulin is not recognized by the antibody.
3. C-peptide-like activity is not determined in HI batch C038.
4. Sample analysis is highly reproducible with the given assay as indicated by the CV values obtained, 3.9% in case of Hlet and 2.97 in case of HI Batch C038.

IV. Specificity of the Assay

The data presented above clearly show that when using the outlined method the assay is only minimally influenced by pure human insulin, which is the prerequisite for the determination of C-peptide-like immunoreactivity in pharmaceutical insulin preparations.

With the help of C-peptide containing model compounds, we investigated the specificity of our antibody in the given assay format. A description of the model compounds is given in the following sections.
1. HI PPI
2. Human C-peptide
   Synthetic human insulin chain C was obtained from Sigma (Cat. # C-5051). The purity is reported to be 97%, the peptide content is 84%.
3. HI reduced/alkylated
   The object is to analyze a linear C-peptide with protected N- and C-terminal ends. This control mimics an unfolded PPI and shows that antibodies binding to the central parts contribute to the specificity of the affinity purified antiserum preparation. The preparation of this control sample is described in Example 4.
4. HI cleaved with endoproteinase Asp-N at the EDP (C6–C7) site of the C-peptide. The purpose is to analyze a human insulin with covalently connected C-peptide sequences on the C-terminus of the B-chain and/or the N-terminus of the A-chain. This control mimics impurities deriving from acid cleavage of the EDP site in the C-peptide. It also mimics putative impurities deriving from incomplete trypsin cleavage. The preparation of this control sample is described in Example 5.
5. HIA2 C-peptide (purification #: HD/19, 21.07.99; purity >99%):
   This C-peptide is truncated on the N-terminal part when compared with HI C-peptide and therefore has lost epitopes on the N-terminus. HIA2 C-peptide can serve as a model for N-terminally cleaved or modified impurities of the isolated HI C-peptide.
6. HIA2 PPI (purification #: UB11/30-HP2; purity 96%):
   Like HIA2 C-peptide, this mutated PPI can serve as a model antigen that helps to monitor immunoreactivities of the antibody with PPI that has a drastically altered C-peptide part, when compared with HI PPI.

The results of the control assays using the described model compounds as well as their interpretation is given in Example 7.

V. Summary Of The Control Experiments

The panel of model compounds excellently delineated the specificities of our affinity purified antiserum preparation 99Ser9.

In view of all the results shown, it can be concluded that the bead assay described in this application is well suited to measuring C-peptide-like immunoactivity in samples from insulin production. Because the antibody preparation in the given assay design recognizes all model compounds, it can be concluded that all major and putative C-peptide impurities in samples from recombinant insulin production most probably can be recognized by the assay.

Example 2

Analysis of the Elimination of Contaminating C-Peptide Containing Impurities During Purification of HI Using the Described Assay of the Present Invention (Comparison with 3 Alternative Assays)

The new immunoassay has been applied to investigate the elimination of C-peptide-like immunoreactivity in 3 different production batches (UA114, UA0115, UA116). Test batch step samples from purification steps 12 (samples SB), 13 (samples KA and KB), and 14 (samples UA) have been analyzed for insulin C-peptide-like immunoreactivity.

The results obtained with the bead assay according to the present invention ("Beads") are compared to the outcome of the commercially available alternative assays:

(1) HMR-RIA ("RIA"), (2) Human C-peptide RIA Kit from Linco Research Inc. ("Linco RIA"), and (3) the ELISA method developed by NewLab Diagnostic Systems GmbH (NewLab").

Short Description of the Assays Used:
(1) RIA (original): radioimmunoassay, based on antibody 99Ser7 affinity purified on immobilized PPI. Monkey C-peptide is used as tracer, HI PPI is used as standard: Range of standard curve: 0.39–25 ng/mL (detection limit: 0.5 ng/mL).
(2) Linco RIA: commercially available radioimmunoassay based on anti human C-peptide antibodies. This assay shows good cross reactivity to monkey C-peptide and PPI, however binding to HI PPI is reduced by a factor of 3 as compared to the bead assay (see Table 9 below). Human C-peptide is used as standard and tracer: Range of standard curve: 0.1–5.0 ng/mL (detection limit: 0.1 ng/mL). This assay is also described in #2 at page 6 above, Human C-peptide RIA Kit (Cat 3 HCP-20K).
(3) NewLab: Sandwich ELISA developed by NewLab Diagnostic Systems GmbH, based on monoclonal anti-human C-peptide (Fitzgerald) and polyclonal anti monkey C-peptide serum. This assay shows strong preference for isolated C-peptide (monoclonal anti human C-peptide and polyclonal anti monkey C-peptide without affinity purification on PPI resins). Monkey C-peptide is used as a standard. Linear range of standard curve: 0.5–10 ng/mL (detection limit: 0.5 ng/mL).
(4) Beads: the assay according to the present invention. The non-radioactive coated bead assay is based on antibodies 99Ser9 obtained after affinity purification on a HI PPI affinity column (like the antibodies in the RIA). Monkey C-peptide is used as standard and tracer. Range of standard curve: 0.39–25.0 ng/mL (detection limit: 0.4 ng/mL).

In the following tables, the following definitions of the abbreviations apply: SB: Test batch step samples after purification step 12 (ion chromatography); KA and KB: Test batch step samples after purification step 13 (RP-Chromatography); UA: Test batch step samples after purification step 14 (final crystallization); ND—not done.

TABLE 5

Data Comparing the Commercially Available Alternative Assays with the Bead Assay of the Present Invention for Probe C 054

| Probe | RIA (1) (ng/mL) | Linco (2) (ng/mL) | NewLab (3) (ng/mg) | Beads (4) (ng/mg) #1 | #2 |
|---|---|---|---|---|---|
| C054 | 0.18 | 0.12 | ND | 0.03 | 0.00 |
| UA-0114-1-01 | 0.06 | 0.10 | <0.5 | 0.00 | 0.00 |
| KB-0114-2-02 | 0.24 | 0.12 | <0.7 | 0.00 | 0.03 |
| SB-0114-2-01 | 1228.75 | 108.77 | 60.00 | 249.00 | 210.00 |
| KA-0114-2-09 | 0.34 | 0.12 | <0.6 | 0.00 | 0.00 |
| SB-0114-1-03 | 691.13 | 78.22 | <50 | 189.00 | 156.00 |
| UA-0114-1-02 | 0.31 | 0.12 | <0.5 | 0.15 | 0.17 |
| KA-0114-2-05 | 0.34 | 0.13 | <0.6 | 0.11 | 0.23 |
| SB-0114-2-04 | 1502.86 | 114.05 | 90.00 | 257.0 | 252.0 |
| KA-0114-2-10 | 0.19 | 0.11 | <0.7 | 0.04 | 0.00 |
| SB-0114-1-04 | 847.36 | 87.60 | 90.00 | 208.00 | 192.00 |
| UA-0114-1-03 | 0.43 | 0.13 | <0.6 | 0.11 | 0.13 |
| KB-0114-2-08 | 0.65 | 0.15 | <0.6 | 0.00 | 0.00 |
| SB-0114-2-06 | 1273.23 | 137.98 | 120.00 | 346.00 | 335.00 |
| KA-0114-2-11 | 0.63 | 0.15 | <0.6 | 0.00 | ND |
| SB-0114-1-05 | 961.21 | 116.83 | 80.00 | 216.00 | 172.00 |
| UA-0114-1-05 | 0.36 | 0.12 | <0.5 | 0.00 | 0.00 |
| KA-0114-2-01 | 0.69 | 0.16 | <0.6 | 0.00 | 0.00 |
| SB-0114-1-01 | 847.67 | 80.65 | 70.00 | 241.00 | 179.00 |
| KB-0114-2-04 | 0.71 | 0.13 | <0.5 | 0.00 | 0.03 |
| SB-0114-1-02 | 1030.86 | 107.76 | 70.00 | 237.00 | 218.00 |
| HI (U103) | 0.36 | 0.13 | ND | 0.05 | 0.19 |

TABLE 6

Data Comparing the Commercially Available Alternative Assays with the Bead Assay of the Present Invention for Probe C 055

| Probe | RIA (1) (ng/mL) #1 | #2 | Linco (2) (ng/mL) #1 | #2 | NewLab (3) (ng/mg) | Beads (4) (ng/mg) |
|---|---|---|---|---|---|---|
| C055 | 0.00 | | 0.13 | | | 0.02 |
| UA-0115-1-01 | 0.77 | 11.04 | 0.17 | 0.50 | <0.5 | 0.00 |
| KB-0115-2-02 | 0.00 | | 0.12 | | <0.5 | 0.00 |
| SB-0115-1-01 | 828.04 | | 78.58 | | 60.00 | 185.00 |
| KA-0115-2-06 | 0.00 | | 0.11 | | <0.5 | 0.00 |
| SB-0115-1-02 | 890.89 | | 78.09 | | 80.00 | 184.00 |
| UA-0115-1-02 | 0.00 | | 0.11 | | <0.6 | 0.27 |
| KB-0115-2-09 | 0.91 | | 0.17 | | <0.5 | 0.07 |
| SB-0115-1-04 | 772.29 | | 75.06 | | 60.00 | 270.00 |
| KB-0115-2-13 | 0.00 | | 0.14 | | <0.5 | 0.01 |
| SB-0115-1-07 | 530.41 | | 54.19 | | 50.00 | 132.00 |
| UA-0115-1-03 | 0.00 | | 0.12 | | <0.6 | 0.05 |
| KB-0115-2-05 | 0.00 | | 0.10 | | <0.5 | 0.00 |
| SB-0115-2-04 | 710.36 | | 67.34 | | 60.00 | 159.00 |
| KA-0115-2-08 | 0.00 | | 0.12 | | <0.5 | 0.00 |
| SB-0115-2-06 | 932.51 | | 65.37 | | 50.00 | 190.00 |
| UA-0115-1-04 | 8.03 | 1.44 | 0.41 | 0.17 | <0.5 | 0.06 |
| KA-0115-2-03 | 0.00 | | 0.12 | | <0.6 | 0.00 |
| SB-0115-2-02 | 661.85 | | 62.54 | | 50.00 | 138.00 |
| KB-0115-2-07 | 0.00 | | 0.14 | | <0.5 | 0.38 |
| SB-0115-2-05 | 726.52 | | 59.09 | | 50.00 | 151 |
| HI (U103) | 0.00 | | 0.11 | | | 0.20 |

TABLE 7

Data Comparing the Commercially Available Alternative Assays with the Bead Assay of the Present Invention for Probe C 056

| Probe | RIA (1) (ng/mL) #1 | #2 | Linco (2) (ng/mL) #1 | #2 | NewLab (3) (ng/mg) | Beads (4) (ng/mg) |
|---|---|---|---|---|---|---|
| C056 | 0.00 | | 0.11 | | | 0.02 |
| UA-0116-1-01 | 0.00 | | 0.14 | | <0.7 | 0.28 |
| KA-0116-1-01 | 0.00 | | 0.11 | | <0.5 | 0.06 |
| SB-0116-1-05 | 1114.96 | | 138.90 | | 90.00 | 333.00 |
| KB-0116-1-02 | 0.13 | | 0.12 | | <0.5 | 0.06 |
| SB-0116-1-06 | 799.15 | | 144.90 | | 80.00 | 417.00 |
| UA-0116-1-02 | 2.90 | 1.28 | 0.30 | 0.18 | <0.7 | 0.07 |
| KA-0116-2-07 | 0.00 | | 0.10 | | <0.5 | 0.62 |
| SB-0116-1-01 | 473.89 | | 76.96 | | <50 | 174.00 |
| KA-0116-2-09 | 7.3 | 0.53 | 0.45 | 0.14 | <0.5 | 0.07 |
| SB-0116-1-03 | 1009.20 | | 112.36 | | 90.00 | 326.00 |
| UA-0116-1-03 | 1.28 | 8.46 | 0.21 | 0.41 | <0.5 | 0.00 |
| KB-0116-2-02 | 0.00 | | 0.09 | | <0.5 | 0.00 |
| SB-0116-2-02 | 224.60 | | 49.35 | | <50 | 194.00 |
| KB-0116-2-06 | 0.00 | | 0.09 | | <0.5 | 0.06 |
| SB-0116-2-07 | 849.40 | | 93.30 | | <50 | 289.00 |
| UA-0116-1-04 | 0.00 | | 0.13 | | <0.6 | 0.39 |
| KA-0116-2-05 | 0.72 | | 0.20 | | <0.7 | 0.08 |
| SB-0116-2-06 | 902.50 | | 92.68 | | <50 | 282.00 |
| KB-0116-2-08 | 0.00 | | 0.14 | | <0.5 | 0.27 |
| SB-0116-1-02 | 517.30 | | 74.22 | | <50 | 98.00 |
| HI (U103) | 0.00 | 0.35 | 0.10 | 0.13 | | 0.28 |

Results:
1. The new immunoassay of the present invention determines the elimination of C-peptide immunoreactivity in in-process control batch step samples of the HI purification process. (See Tables 5–7, last column—Beads (4)). Because C-peptide is used as a standard, values obtained from the present invention are about 2.5–3 times lower than with the original RIA (See (1) above as compared to (4)). In fact, a four-fold difference was found (mean value), which correlates directly with the drastically reduced incubation time when compared with the RIA.
2. C-peptide-like immunoreactivity is not detectable in HI end probes with the coated bead assay of the present invention. The calculated concentrations are in the range of the values that can be measured for HIet. The mean values of KA/KB and UA samples are:
   104.7±3.7 (CV=3.5%) for samples from KA/KB 114 (n=8).
   103.8±5.3 (CV=5.1%) for samples from KA/KB 115 (n=8).
   99.8±3.7 (CV=3.7%) for samples from KA/KB 116 (n=8).
   102.3±3.7 (CV=3.6%) for samples from UA 114 (n=4).
   100.3±3.2 (CV=3.2%) for samples from UA 115 (n=4).
   99.1±3.8 (CV=3.8%) for samples from UA 116 (n=4).
   All these values exactly fit to the variation range as determined by repeated measurement of Hlet.
3. The data shown in the last column of Table 5 (Beads (4)) make it clear that the assay of the present invention yields reproducible results.
4. The original RIA (1) suffers from "runaways," results obtained in identical samples after repeated analysis that are not consistent or comparable with the result first obtained and cannot be explained by obvious faults in sample handling or assay performance. In addition, the assay is characterized by poor reproducibility. (See Tables 6 and 7, bold values).
5. The Linco RIA (2) is much more robust than the original RIA (1) and reproducibility is improved. Like the original RIA, this assay also suffers from the sample dilution method, although not as seriously as the original RIA (See Tables 5–7). Since the Linco RIA is the most sensitive assay variant tested, a trace amount of insulin C-peptide-like activity in the concentration range between 0.1–0.5 ng/mL can be detected in some end product samples.

6. In the assays RIA (1), Linco (2), and Beads (4), HIet routinely has been introduced as control (See Tables 5–7). In theory, the HIet value can be subtracted from all results showing that indeed there is no, or only a minute amount of, insulin C-peptide immunoreactivity present in most of the final batch step samples of insulin purification.

7. The NewLab ELISA does not produce clear results, because the background is determined with the test batch step sample itself (not with HIet). In addition, the assay is dominated by the affinity of the monoclonal anti-human-proinsulin-C-peptide antibody (clone M607239; cat/lot no. FZ10-C65) for which the extent of cross reactivity to PPI is not known. There are no data showing how strong the interaction with PPI is in the NewLab assay. In consequence to the assay design (principally designed to analyze C-peptide) low values—even lower than in the Linco assay—of C-peptide immunoreactivity (if any) can be measured in "source samples". An alternative explanation for this fact could be that samples are not dissolved very well at the working pH. However a proof of total dissolution is not demanded in the specific standard operating procedure of the NewLab ELISA protocol.

Conclusion

The described new immunoassay of the present invention is very well suited for analyzing the elimination of C-peptide-like immunoreactivity in in-process control batch step samples from human insulin production with high sensitivity, precision, and good reproducibility (CV<5%).

The minimal concentration of insulin C-peptide-like activity that can be detected with the assay of the present invention is 0.4 ng/mL. Thus, all values below this value are considered background noise and should not be expressed numerically.

The Merits of the New Assay are:
  It is a non-radioactive assay using a chemiluminescent label.
  The tracer is very stable. Thus identical tracer material can be used for a long time (approximately 20 weeks without loss of quality). Comparable and stable assay conditions over long time periods are a prerequisite for routine applications and long term comparability of results.
  Total assay time is only 5 hours. No specific preparatory work is needed. The assay can be performed within 1–2 days after sample arrival.
  It is a homogenous assay without sequential steps or intermediate washes. More than 50 different probes can be analyzed on the same day.
  No sophisticated technical equipment is necessary to perform the assay.
  The assay is cheap (no routine labeling, no radioactive equipment, no radioactive waste, only standard labware is needed).
  The assay principle is simple so that technical staff with no specific experience can be trained to perform the analysis very quickly.
  Sample dilution is a simple two-step process without the need for subsequent pH measurements and adjustments. The sample remains dissolved during the whole incubation time. This holds true for HI, HIA1 end products, and all intermediate batch step samples of down stream processing. This cannot be achieved with any of the alternative assays.
  The assay is robust with a repeatability of 4% (see Table 1) and an inter-assay variability of 4% (see Table 4). Both values are calculated on the basis of the raw B/B0-data.
  Both HI probes and HIA1 probes can be analyzed using the same assay protocol, ingredients, and buffers (see Tables 5–8).
  HIA2 C-peptide-like immunoreactivity can be analyzed with a cutoff of 10 ppm (detection limit) using the same assay protocol, ingredients, and buffers.
  The assay may be converted to a coated tube format or to micro-well format when using special tubes or micro plates. In this way, purchase of the second antibody beads can be avoided.
  The sensitivity of the assay can be improved by increasing the incubation time or by using more concentrated antibody and tracer, allowing reduced volumes of both.
  The only assay with an exact description of its specificity.

Example 3

Purification Of Sheep Anti Monkey Insulin C-Peptide Antibodies for Use in Immunoassays to Quantitate "Preproinsulin Like Activity"

Preparation Of Affinity Resins

I. Coupling of Human Insulin to Fractogel EMD Azlacton 650 (S)

A. Conditioning Of The Resin 7 g of Fractogel EMD Azlacton 650 (S) was allowed to swell for 15 minutes in 140 mL PBS, pH 7.4. After this incubation the supernatant was removed by passing through a glass filter. The remaining gel (about 24 mL) was suspended in 20 mL PBS, pH 7.4.

B. Dissolving Of Human Insulin 120 mg semisynthetic human insulin (insulin ET [insulin HPU, HGR, IE Sap. Nr.: 116312, Muster A48, Ch.-B.: U118]) was dissolved in 3 mL 50 mM phosphoric acid. The solution was slowly dropped into 50 mL PBS pH 9.4 with stirring. The pH dropped to 6.65 at the end of this procedure. Finally, the pH of the insulin solution was adjusted to 7.4 by careful addition of 2M NaOH.

C. Coupling Reaction

The insulin solution and the conditioned gel were mixed and the coupling reaction via the functional Azlacton was allowed to proceed at ambient temperature. A constant and careful mixing was achieved by slow head forward rotation of the reaction beaker. After 4 h at ambient temperature, the supernatant with unreacted ligand was filtered off and the gel was washed with 120 mL PBS. The HPLC analysis resulted in 67 mg of unbound human insulin. Consequently, 53 mg had been covalently immobilized on the EMD Fractogel.

Remaining active groups on the resin were blocked by addition of 120 mL 0.2 M glycine, pH 8.0. The reaction was allowed to proceed at ambient temperature. Again a constant and careful mixing was achieved by slow head forward rotation of the reaction beaker. After 16–20 h the supernatant with unreacted glycine was filtered off and the gel was washed with three cycles of 120 mL PBS pH 7.4, 0.1 M sodium acetate, 0.2 M glycine pH 2.8, each.

The resulting affinity resin with covalently coupled human insulin was suspended in PBS, pH 7.4, with 0.04% Proclin as preservative and poured into an HR 16/15 FPLC column.

II. Coupling of Human PPI to Fractogel EMD Azlacton 650 (S)

A. Conditioning of the Resin 14.5 g of Fractogel EMD Azlacton 650 (S) was allowed to swell for 15 minutes in 290 mL PBS, pH 7.4. After this incubation the supernatant was removed by passing through a glass filter. The remaining gel (about 50 mL) was suspended in 20 mL PBS, pH 7.4.

B. Dissolving of PPI 250 mg PPI was dissolved in 6 mL 50 mM phosphoric acid. The solution was slowly dropped into 100 mL PBS pH 9.4 with stirring. The pH dropped to 6.60 at the end of this procedure. Finally, the pH of the PPI solution was adjusted to 7.4 by careful addition of 2M NaOH.

C. Coupling Reaction

The PPI solution and the conditioned gel were mixed and the coupling reaction via the functional Azlacton was allowed to proceed at ambient temperature. A constant and careful mixing was achieved by slow head forward rotation of the reaction beaker. After 4 h at ambient temperature, the supernatant with unreacted ligand was filtered off and the gel was washed with 120 mL of PBS. The HPLC analysis resulted in 67 mg of unbound PPI. Consequently, 171 mg had been covalently immobilized on the EMD Fractogel.

Remaining active groups on the resin were blocked by addition of 250 mL 0.2 M glycine, pH 8.0. The reaction was allowed to proceed at ambient temperature. Again, a constant and careful mixing was achieved by slow head forward rotation of the reaction beaker. After 16–20 h the supernatant with unreacted glycine was filtered off and the gel was washed with three cycles of 250 mL PBS pH 7.4, 0.1 M sodium acetate, 0.2 M glycine pH 2.8, each.

The resulting affinity resin with covalently coupled PPI was suspended in PBS pH 7.4 with 0.04% Proclin as preservative and poured into a XK 26/20 FPLC column.

III. Purification of Anti Insulin C-Peptide Antibodies By Affinity Chromatography A. Preparation of the Serum The source for antibody purification was a serum from sheep S95-11, which was immunized with purified monkey insulin C-peptide. The serum had been stored at −20° C. until thawing. After thawing, the total volume of the serum was determined to be 79 mL. The volume was doubled by adding 65 mL water and 16 mL PBS (10× concentrated, plus 0.4% Proclin) to adjust the buffer conditions for chromatography. The diluted serum was subsequently centrifuged at 26,000×g for 30 minutes at 4° C. The supernatant was filtered through stacked 5 μm and 0.2 μm membranes protected by a glass filter layer.

B. Affinity Chromatography

The rationale for the purification scheme was to remove antibodies that nonspecifically bind to the EMD Fractogel resin and sequences in human insulin as well as putative sheep anti-insulin antibodies in a first step by passing the serum through the human insulin affinity resin.

In a second step anti-monkey insulin C-peptide antibodies can be purified after their binding to the C-peptide, which is an integral part of PPI immobilized on EMD Fractogel.

Affinity chromatography on PPI was chosen (instead of chromatography on immobilized C-peptide), because in order to use the purified antibodies in an immunoassay for quantification of PPI-like immunoreactivity, binding to C-peptide and/or C-peptide fragments still connected to the insulin moiety is a prerequisite.

IV. Purification Protocol

A. Sample Application

The diluted sheep serum was pumped through the two affinity columns (flow: 3.5 mL/min) in one step by directly connecting the human insulin EMD Fractogel HR16/11 column ("first column") to the PPI EMD Fractogel XK26/11 column ("second column"). The first column eliminates all undesired binders, but does not interact with anti-insulin C-peptide antibodies. The second column specifically binds anti-monkey insulin C-peptide antibodies.

Nonspecific sheep antibodies, as well as serum components, cannot interact with the affinity resin of the second column and thus, flow through the column into the eluate. Total capture of specific antibodies by the affinity column was checked by analysis of the flow-through making use of the BIACORE® system. In the flow-through fraction, there was no binding activity detectable.

B. Elution

After passage of the serum, the two columns were disconnected and independently eluted with 0.1 M glycine, 0.04% Proclin pH 2.7 (flow: 5 mL/min).

In the case of the first column, the acidic elution directly results in regeneration of the affinity matrix, which can subsequently be conditioned by extensive equilibration with PBS buffer.

Figure 4A:
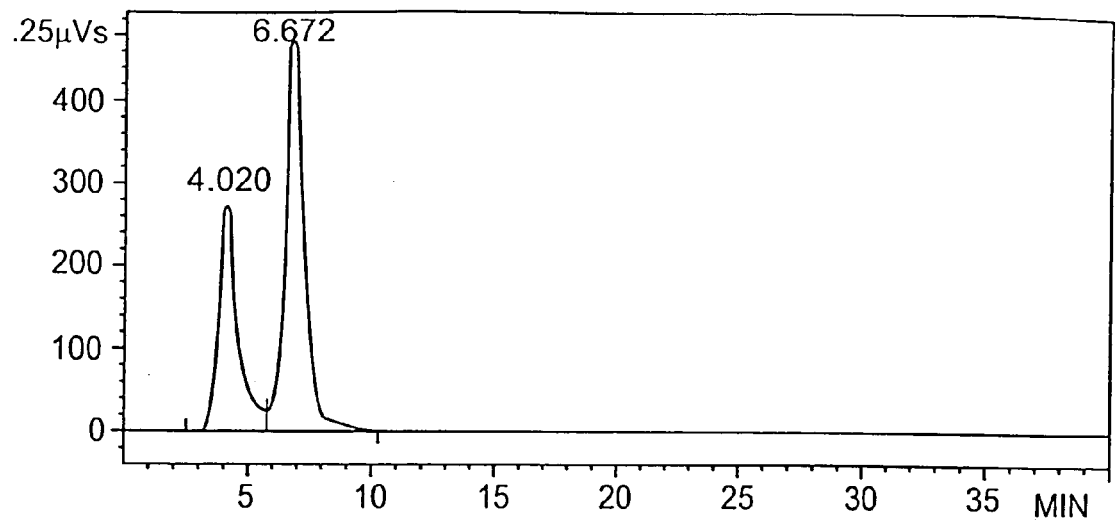
FIG. 4 A depicts the elution profile of a human insulin obtained from an Azlacton HR 16/11 column.
Figure 4B:
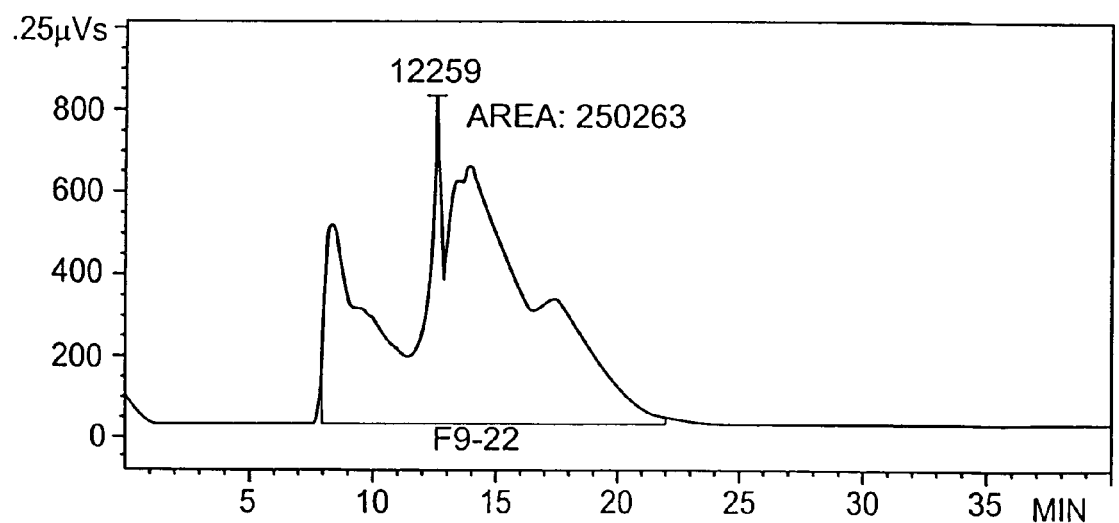

FIG. 4A depicts the elution profile of a human insulin chromatographed on an Azlacton HR 16/11 column. The elution profile of the PPI EMD Azlacton column is shown in FIG. 4B. Fractions 9–22 contain active anti-monkey insulin C-peptide antibodies as analyzed with the BIACORE® system. The indicated fractions were pooled and concentrated to 10 mL using Amicon Ultrafree-15 units (10 kDa molecular weight cut off membranes).

Figure 5:
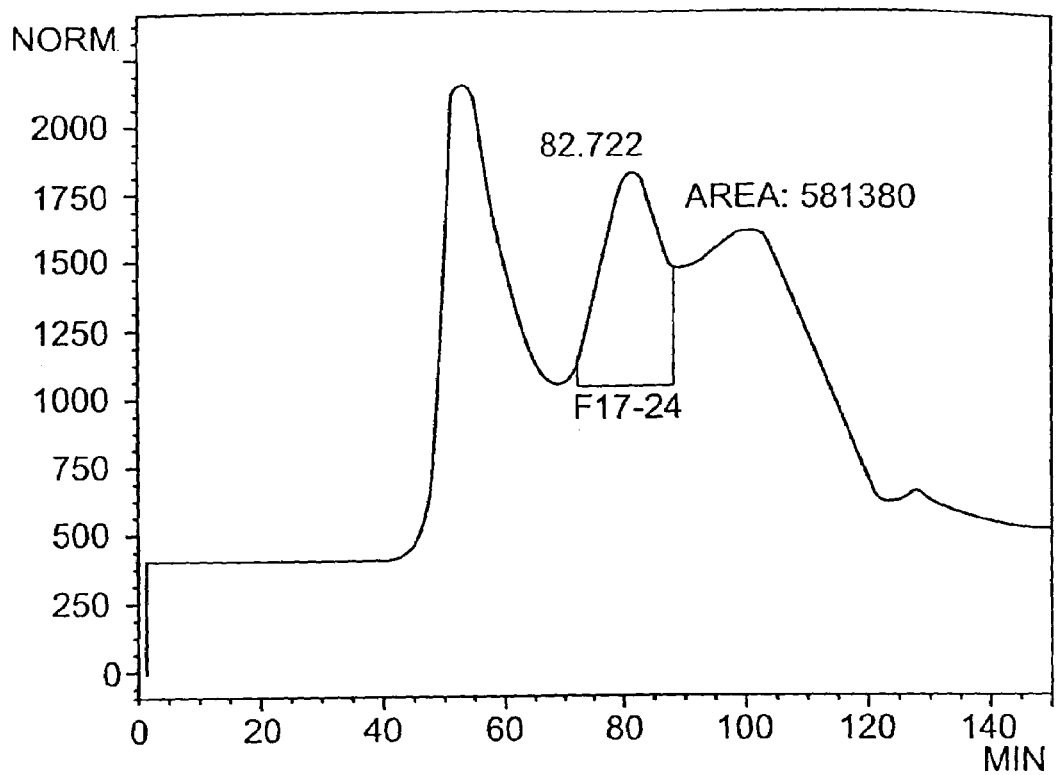
FIG. 5 depicts the elution profile of the concentrated glycine eluate containing anti-monkey insulin C-peptide antibodies obtained from the previous column (PPI EMD Fractogel column). This eluate was chromatographed on a Superdex 200 (26/60) exclusion column.
Figure 6:
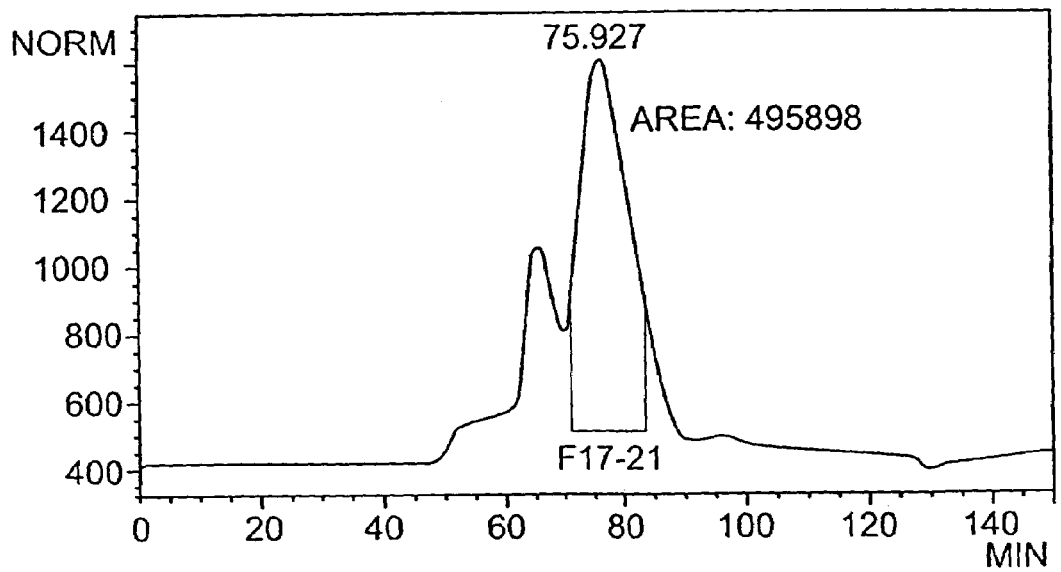
FIG. 6 depicts the elution profile obtained from a second gel filtration chromatography of fractions 17–24 obtained from the Superdex 200 (26/60) exclusion column. To achieve higher purity the same column was used.

To further purify the antibodies and to transfer them into a neutral buffer, the concentrated glycine eluate was chromatographed on a Superdex 200 (26/60) size exclusion column. The elution profile is shown in FIG. 5. Fractions 17–24 contain the purified sheep anti monkey insulin C-peptide antibodies. To achieve higher purity of the antibodies, a second gel filtration chromatography was performed using the same Superdex 200 (26/60) column (FIG. 6). The protein eluting in fractions 17–21 was pooled and stored as the final antibody preparation "99Ser9-rechr".

The flow-through of the affinity tandem column as well as the eluants of the PPI EMD Fractogel and Superdex 200 columns were analyzed using the BIACORE® system. This technique allows the fast detection of anti-monkey insulin C-peptide antibodies by simulation of the affinity chromatography in a 60 nL flow cell generated on the surface of a sensor chip. Active antibodies binding to PPI immobilized in this flow cell can be detected by surface plasmon resonance with high sensitivity.

Results:

The volume of the antibody preparation was 24 mL as determined with a graduated cylinder. Protein concentration was determined by the BCA method in a micro well format according to the instructions of the supplier (Pierce). The OD at 560 nm was measured using a Spectra III Elisa reader (SLT).

A standard curve with IgG of known concentrations was used to calculate the unknown concentration of the antibody preparation. The mg/mL value of the unknown was read directly from the plotted data.

The described antibody preparation had a concentration of 0.454 mg/mL. The total yield of antibody was 10.9 mg. The antibody preparation was aliquoted in 1 mL portions, each labeled with 99Ser 9/rechr.F17-22, and stored at −70° C.

Conclusions

The above described antibody preparation (99Ser 9/rechr.F17-22) can be used in immunoassays to quantitate insulin C-peptide-like immunoreactivity, especially in the assay variant coated bead chemiluminescence assay.

Example 4

Alkylation of Human PPI (Batch 216-1):

3.28 mg of PPI was dissolved in 109 μL $H_2O$ and further diluted by adding 109 μl 10-fold concentrated PBS buffer supplemented with 0.4% Proclin. Finally, a solution was prepared with a PPI content of 3 mg/mL by adding 875 μL $H_2O$. To 990 μl of this PPI solution, 10 μL of 1M DTE (in water) was pipetted. The sample was incubated at 37° C. for 5 hours. After 1 h reaction time, precipitation of protein was detectable and still present after raising the pH to 9.0 for the remaining time.

To stop the reduction of S—S bridges in PPI and to protect free sulfhydryl from reoxidation and/or generation of new S—S bonds, 185 mg of solid iodoacetamide was added and incubated 4 hours in the dark at 4° C.

The resulting alkylated PPI was then dialyzed twice against 400 mL PBS, 0.04% Proclin in a Tube-O-Dialyser. The precipitated protein was removed by centrifugation. In the clear supernatant (1.3 mL), 23 μg/mL of soluble alkylated PPI could be determined by amino acid analysis after hydrolysis of the sample.

A slightly retarded penetration in SDS-gel electrophoresis amino acid analysis and a better susceptibility to proteolytic degradation with endoproteinase Asp-N (See Example 6) proved the effective derivatization. Obviously, endoproteinase Asp-N cleaves the reduced PPI at the derivatized cysteines, in addition to the DP-site.

Example 5

Cleavage of Human PPI at the EDP site with Endoproteinase Asp-N

Endoproteinase Asp-N is a metallo-protease that specifically cleaves peptide bonds N-terminally at aspartic and cysteic acid. Human PPI (HIA1 PPI) contains only one aspartic acid in its sequence. It is located in the C-peptide where it is situated N-terminally to a proline residue, creating the acid labile DP (C6–C7) site. This site presumably is located on the outer surface of the PPI molecule and should therefore be accessible to endoproteinase Asp-N. The cysteine residues all are involved in S—S bridges, buried within the molecule and therefore protected from proteolytic attack. By splitting PPI at the EDP site, a valuable model compound can be generated helping in delineating the specificity of our affinity purified antibodies.

To cleave the EDP site within the C-peptide 50 μl of PPI (0.7 mg/mL in water) and 50 μl of 50 mM Tris/HCl pH 8.0 containing 0.2 M urea were mixed. Proteolysis was started by the addition of 25 μl endoproteinase Asp-N (1 μg dissolved in 10 mM Tris-HCl, pH7.5) and was incubated for 32 hours at 37° C. The reaction was stopped by freezing the sample.

Gel electrophoresis and subsequent silver staining showed that PPI was quantitatively cleaved at the EDP site because two bands can be separated after reduction of the disulfide bonds in the enzymatically cleaved protein (See Example 6). There is no remaining protein band visible at the position of uncleaved reduced PPI (which still is a single chain molecule).

The endoproteinase Asp-N cleaved PPI can serve as a model (control) compound that:
mimics an impurity resulting from acid cleavage of the EDP site,
mimics an insulin derivative resulting from incomplete trypsin cleavage with parts of the C-peptide still connected to the C-terminus of the A-chain and/or on the N-terminus of the B-chain.

Example 6

Analysis of HI and HI Reduced/Alkylated, as Well as the Endoproteinase Asp-N Cleaved Products Thereof with SDS Gel Electrophoresis (4–12%)

Figure 7:
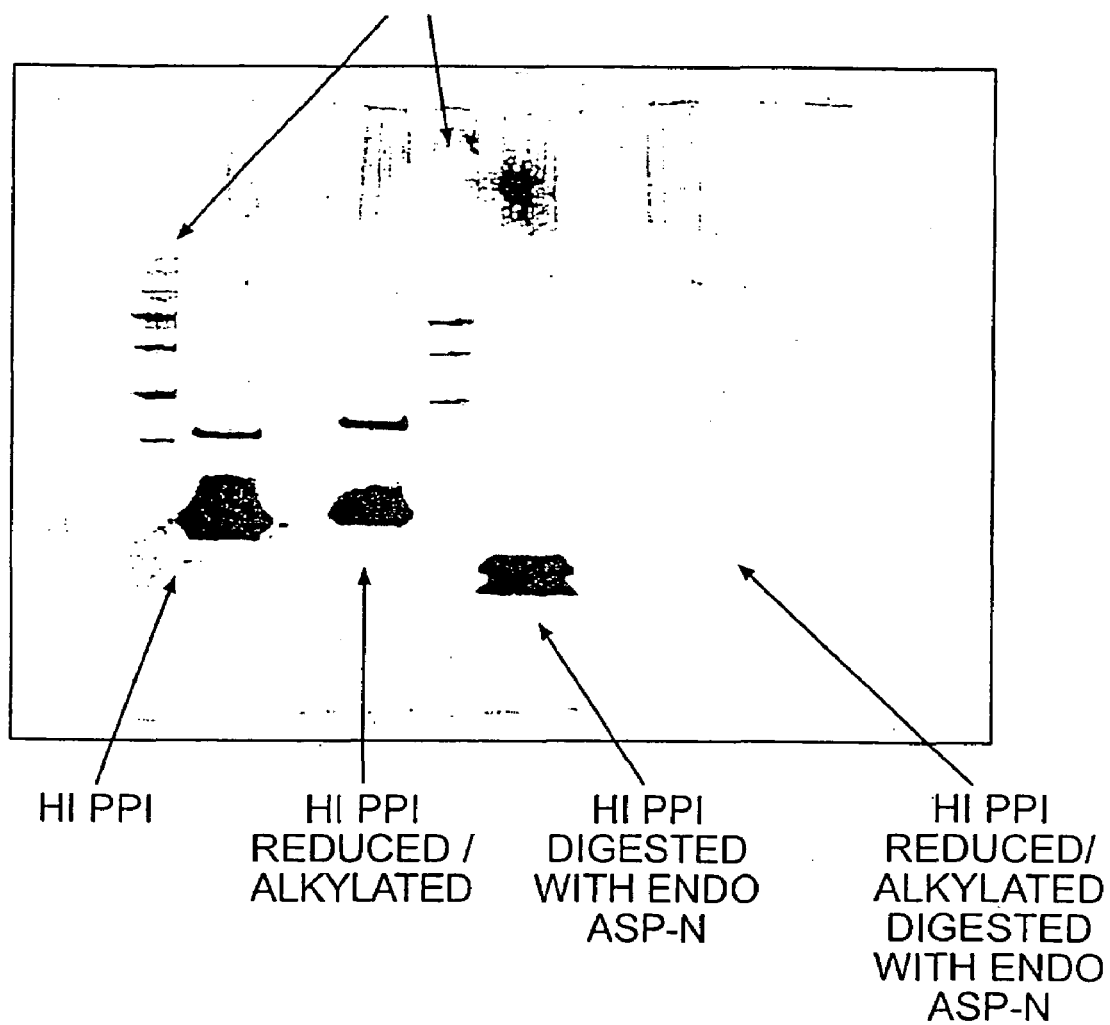
FIG. 7 depicts an SDS gel analyzing the susceptibility of HI HI reduced/alkylated to endoproteinase Asp-N cleavage. The samples contained DTE to reduce any disulfide bridges.

The samples were applied to an electrophoresis gel in SDS-buffer containing DTE to completely reduce the S—S bridges. See FIG. 7.

Example 7

Figure 8:
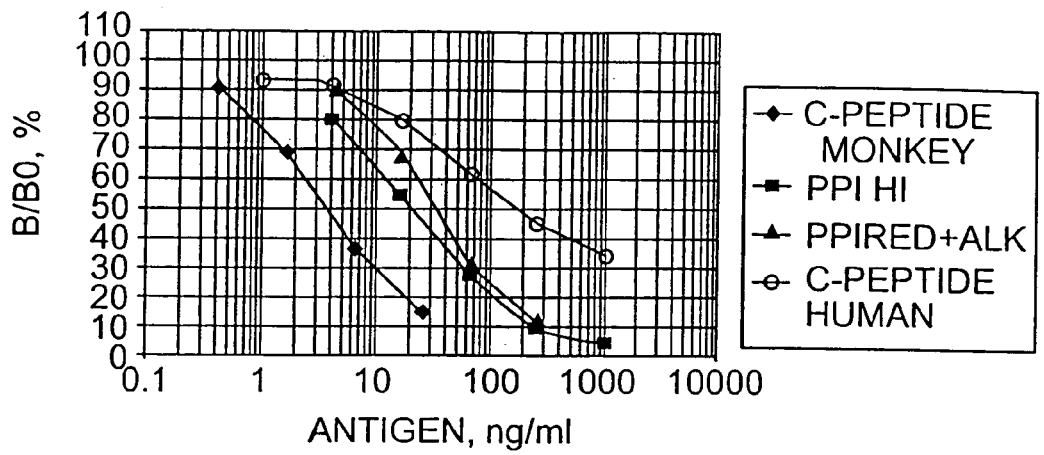
FIG. 8 depicts the analysis of control antigens HI PPI, human C-peptide, monkey C-peptide, and PPI reduced/alkylated using the coated bead assay procedure of the present invention. The 99Ser9 preparation served as the antiserum.
Figure 9:
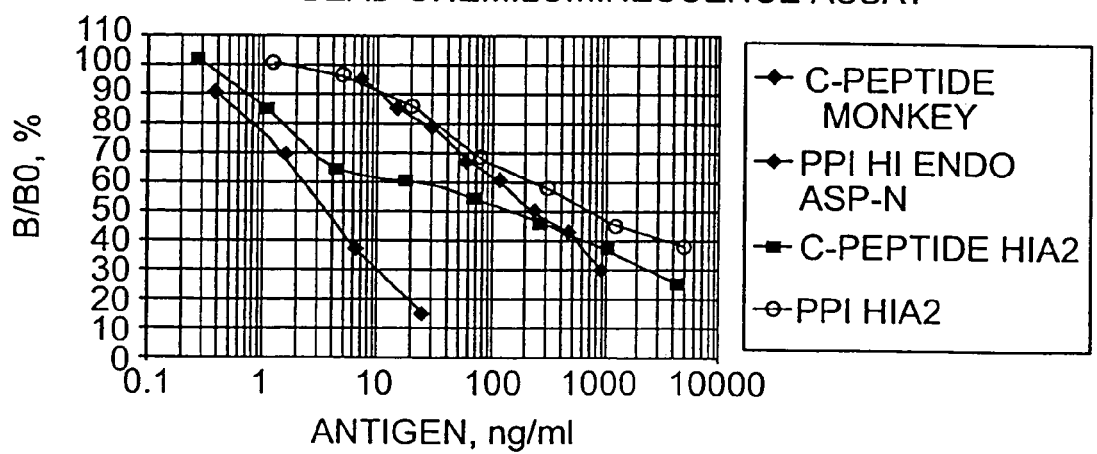
FIG. 9 depicts the analysis of control antigens monkey C-peptide, HI PPI cleaved with endoproteinase Asp-N, HIA2 PPI, and HIA2 C-peptide using the coated bead assay procedure of the present invention. The 99Ser9 preparation served as the antiserum.

Specificity of the Affinity Purified Antibodies From Sheep S95-11 in the Described Assay Format 1. Analysis of HI PPI, HI (monkey) C-peptide, PPI reduced/alkylated, and HI C-peptide using the assay as described in this application (based on preparation 99Ser9). All compounds were diluted in dilution buffer containing 1 mg/mL HIet. For results, see FIG. 8.
2. Analysis of HI (monkey) C-peptide, HI PPI cleaved with Endoproteinase Asp-N, HIA2 PPI, and HIA2 C-peptide using the assay as described in this application (based on preparation 99Ser9). All compounds were diluted in dilution buffer containing 1 mg/mL HIet. For results, see FIG. 9.

Results and Interpretation:

1. HI C-peptide and HI PPI are recognized equally by the antibody as indicated by the parallel dilution relationships and a right shift (factor ~6) of the curve that depends on the difference in the molecular weights and a drastically reduced incubation time (see below, Table 8).
2. Human C-peptide is recognized by the assay, but about 180 ng/mL is needed to obtain 50% inhibition. This is a 55-fold higher concentration as compared to monkey C-peptide. These data clearly illustrate the high specificity of the antibody preparation to the monkey C-peptide, which differs from the human sequence only at amino acid 37 (Pro vs. Leu) (see Table 8).
3. There is a distinct cross reactivity to Endoproteinase Asp-N cleaved PPI. However, the dilution curve is wavy and there is an ~10-fold loss of reactivity compared to native PPI (see Table 8). This indicates that structural epitopes are destroyed by introducing a single split into the C-peptide and that the EDP site is a major immunogenic epitope that is recognized by the 99Ser9 antibody preparation.

4. Alkylated PPI is recognized without significant loss of immunoreactivity indicating that antibodies specifically recognizing the N- and C-terminal amino acids could be removed by affinity chromatography so that they cannot influence the specificity of the antibody preparation. Because alkylated PPI mirrors a linear C-peptide with the size of PPI, the dilution curves of PPI and PPI reduced/alkylated are more or less superimposable.

5. A pronounced flattening of the dilution curves is seen with HIA2 C-peptide and HIA2 PPI where the epitopes on the N-terminal part of the C-peptide are eliminated and mutated. The antibody 99Ser9, however, still binds to these antigens with an affinity that is reduced about 35 fold as compared to the respective structures of HI PPI. The wavelike behavior of the dilution curves is typical for situations where different populations of monospecific antibodies (as in a polyclonal serum) react with antigens with related but not identical epitopes. The fast decline in the inhibition curve at low antigen concentrations depicts the interaction of antibodies to the (non altered) C-terminal part of the linear C-peptide. The flat phase of the curve indicates that a substantial amount of antibodies binds with reduced affinity to the central and N-terminal parts of HIA2 C-peptide, which are mutated and structurally changed as compared to HI PPI. These related antigens cannot displace the tracer (labeled HI C-peptide) from the antibody as effectively as the HI antigens.

6. PPI HIA2 and PPI HI cleaved at the EDP site are recognized nearly equally by the assay, again showing the importance of the EDP site in immune recognition by antibody preparation 99Ser9. Concentrations $\geq 10$ ng/mL of these or related antigens positively can be detected using the given assay.

In the original RIA (1) and in the Linco assay (2) (See Example 2 above), the concentrations have to be on the order $\geq 20$, ng/mL. It is not possible to give respective data for the ELISA developed by NewLab (3), because the controls were not performed and there is no data about the detection limit of PPI using this method. Deduced from the assay design, it can be anticipated that the ELISA would show lower levels of cross reactivity to PPI and PPI-derivatives than the Linco assay.

TABLE 8

IC50-Values Obtained With Different Inhibition Assays And Different Antigens

| IC50 | Bead assay ng/mL | HMR-RIA * ng/mL | Linco assay ng/mL |
|---|---|---|---|
| C-peptide (human) | 180.0 | n.d. | 1.0 |
| C-peptide (monkey) | 3.2 | 1.0 | 1.0 |
| HI PPI | 20.0 | 4.0 | 60.0 |
| PPI, cleaved at EDP-site | 200.0 | 100.0 | 300.0 | n.d.: not determined
* it has to be taken into consideration that the variance in this method is >5-times higher than in the Bead assay or Linco assay, thus limiting the value of the data given in the Table.

Summarizing all the results obtained with the model compounds it clearly can be stated that the antibodies obtained from sheep S95-11 preparation 99Ser9 (and 99Ser7 which is used in the RIA) fulfill the requirements to positively identify different kinds of C-peptide containing antigens, which can be circumscribed with "C-peptide-like immunoreactivity".

Example 9

Analysis Of In-Process Batch Step Samples From Insulin HIA1 Production—Elimination of Insulin Like Immunoreactivity During Down Stream Processing.

TABLE 9

| Sample, code | | | C-peptide-like activity, ng/mL |
|---|---|---|---|
| Step 8 | 901/8 | A003 | 15800 |
| | | B003 | 15980 |
| | | C003 | 17480 |
| Step 9 | 901/9 | A006 | 13540 |
| | | B006 | 15320 |
| | | C006 | 13660 |
| Step 10 | 901/10 | A008 | 138100 |
| | | B008 | 135720 |
| | | C008 | 164260 |
| Step 11a | 0055 | APK 02 | 5808 |
| | | APK 03 | 4424 |
| Step 11/12 | 0055 | API 02 | 5574 |
| | | API 03 | 4310 |
| Step 11/12 | 0055 | AHP 01 | 5578 |
| | | AHP 02 | 6901 |
| | | AHP 03 | 5300 |
| Step 12/10 | 0055 | AKR 01 + 02 | 1.07 |
| | | AKR 03 | 0.4 |

Example 10

Immunization and Sampling of Sera From a Sheep (S95/11) with Polyclonal Antibodies Directed Against Monkey C-Peptide This example describes and documents the immunization and sampling of sera from a sheep, containing antibodies directed against C-peptide from monkey.

A female sheep was purchased from Gerhard Mundschenk (Zwerggasse 2; 65468 Trebur-Astheim) and maintained on normal standard diet for goat on a farm (Hermann Kettenbach, Im Birkenfeld 38, 65719 Hofheim-Langenhain). The sheep was marked S95/11.

At the beginning of immunization, the sheep (marked S95/11) was immunized with antigen (initially 2 mg monkey C-peptide) in equivalent volumes (1:1 mixture of 1 mL saline +1 mL complete Freund' adjuvant (cFA; Difco Laboratories, Detroit, Mich., USA)). This emulsion was prepared immediately prior to administration and was injected subcutaneously at 2–3 sites. Booster injections at 2–4 week intervals consisted of the same amount of antigen (2 mg C-peptide) in a 1:1 mixture of saline (1 mL) and 1 mL of incomplete Freund's adjuvant (Sigma Chemicals, Heidelberg, Germany). At intervals of 2 weeks to 2 months, blood samples were taken by puncture of jugular vein. The antiserum was aliquoted and stored at −20° C. until further use. Specified samples were selected for development of an assay for detection of PPI in the final insulin product.

Recombinant human insulin is produced from a fusion protein expressed in transfected E. coli. During the processing of human insulin from the denatured fusion protein the so-called PPI is formed as an intermediate. The latter is further processed by enzymatic trypsin-catalyzed cleavage. The two chain heterodimeric insulin is formed from the single chain PPI by synchronous cleavage at the sequence positions -Arg-Arg-(B31-32) and -Lys-Arg-(A-1-A0). Insulin is produced via further purification processes. For development of an immunoassay for detection of impurities of PPI (<10 ppm) in the final product polyclonal antibodies directed versus C-peptide are particularly suited because there is no interfering cross-reactivity from insulin. In contrast, in the case of immunization with PPI as antigen, the major amount of antibodies would be directed against insulin. The latter would not be suited to detect minute amounts of <10 ppm PPI in the presence of a $10^6$ fold excess of insulin.

To avoid immunogenic insulin-like determinants in the C-peptide used, like -Lys or -Lys-Arg- at position 34 or 34–35 of the C-peptide, monkey C-peptide without these basic amino acids Arg- has been prepared and used as monkey C-peptide.

The immunization procedure including the switch from initial use of cFA to iCA and time scheme corresponds to standard methods as described in the literature for production of polyclonal antibodies directed versus specified antigens and peptides.

Documentation of the immunization scheme and blood sampling for preparation of antisera with polyclonal antibodies against monkey C-peptide in a sheep are presented. The amount of antigen (monkey C-peptide) was dissolved in a 1:1 mixture of 1.0 mL 0.9% saline and 1 mL adjuvant, respectively. Dates of blood sampling are listed. The antigen used in the following study was monkey C-peptide; Lot no.:DJIII,-S43. The initial adjuvant used was KFA (Difco) Lot 70052LA. The adjuvant Booster was IFA (Sigma) Lot 96H8950.

TABLE 10

Immunization scheme

| S95/11 | Date Oct. 2, 1998 Initial Appl. | Date Oct. 22, 1998 Booster: 1 | Date Nov. 12, 1998 Booster: 2 | Date Nov. 12, 1998 Booster: 3 | Date Jan. 11, 1999 Booster: 4 | Date Feb. 11, 1999 Booster: 5 | Date Mar. 11, 1999 Booster: 6 |
|---|---|---|---|---|---|---|---|
| C-peptide (mg) | 2 mg | 2 mg | 2 mg | 2 mg | 2 mg | 2 mg | 2 mg |
| Saline/ adjuvant (mL/mL) | 1.0/1.0 | 1.0/1.0 | 1.0/1.0 | 1.0/1.0 | 1.0/1.0 | 1.0/1.0 | 1.0/1.0 |

TABLE 11

Blood Sampling And Volume Of Sera for S95/11

| Date | Nov. 2, 1998 | Nov. 23, 1998 | Dec. 21, 1998 | Jan. 25, 1999 | Feb. 11, 1999 | Feb. 22, 1999 | Mar. 22, 1999 | Apr. 8, 1999 |
|---|---|---|---|---|---|---|---|---|
| Serum (mL) | 3.5 | 3.8 | 4.0 | 4.0 | 70.0 | 88.0 | 78.0 | 118.0 |

BIBLIOGRAPHICAL REFERENCE FOR EXAMPLE 10

1. Cußler, K., Hartinger, J.: Gibt es Alternativen zum Einsatz von Freundschem Adjuvans bei der Immunisierung von Labortieren? Tagungsabschnitt "Immunisierung und Adjuvantien" des 4. Österreichischen Internationalen Kongresses über "Ersatz- und Ergätnzungsmethoden zu Tierversuchen in der biomedizinischen Forschung", 24–26. Sep. 1995 (Linz).
2. Bennett, B., Check, I. J., Olsen, M. R., Hunter, R. L.: A comparison of commercially available adjuvants for use in research. J. Immunol. Meth. 153, 31–40, 1992.
3. Finger, H.: "Das Freundsche Adjuvans-Wesen und Bedeutung". In: G. Heyman (Ed.): Arbeiten aus dem Paul-Ehrlich-Institut, dem Georg-Speyer-Haus und dem Ferdinand-Blum-Institut zu Frankfurt a.M., Heft 60, Gustav Fischer Verlag, Stuttgart, 1964.
4. Fineberg, S. E., Galloway, J. A., Fineber, N., Goldman, J.: Effects of species origin, purification levels and formulation on insulin immunogenicity. Diabetes 32, 592, 1983.

Example 11

Sample Preparation

It is known that insulin is relatively insoluble in neutral solutions after crystallization or freeze-drying. In order to obtain high concentrated insulin solutions, insulin probes therefore must first be dissolved in acid (e.g., diluted phosphorous acid or HC, either) and afterwards an alkaline pH (9.0–10.5) has to be adjusted by fast addition of the appropriate amount of NaOH. The working pH is then adjusted by titration or by adding respective buffers. This outlined procedure is very time consuming, fussy, and requires individual care for each probe.

To circumvent this ceremonious procedure we tested different protocols for insulin dissolution. The aim was to obtain clear insulin solutions with a concentration of 1 mg/mL and a pH of 8.6–9.0.

A pH >9 is favorable to keep HIA1 and insulin in process batch step samples (especially those after trypsin—cleavage) in solution (the IP of HIA1 is 7,4).

A pH <9.0 is favorable to allow high affinity and stable antigen antibody interactions.

We tested different buffers suitable in the pH range 8.0–9.5 in order to screen for stable antigen (HI PPI)/antibody binding at pH 9.0. Buffers tested were: Tris, TAPS, Bicine, GlyGly, BisTrisPropane, Ches, Phosphate/EDTA (as used in the human C-peptide RIA Kit from Linco Research Inc.).

In addition, different buffer concentrations have been analyzed showing that increasing the buffer concentrations at the given pH 9.0 results in a gradual disturbance of antigen/antibody binding.

In view of the previous discussion, we selected four buffers at a concentration of 20 mM for final comparison:

1. Tris* (Merck-108382),
2. TAPS** (Sigma T-5130),
3. Bicine*** (Sigma B-3876)
4. GlyGly**** (Calbiochem 3630).

We prepared these buffers by dissolving the needed amount of solid in water and adjusted the pH to 9.0 by adding the appropriate amount of NaOH. All show good antigen/antibody binding in the pH-range of about 8.5 to about 9.0.

About 0.5 mg–0.8 mg of insulin samples were dissolved in 10 mM HCl resulting in a 10 mg/mL solution. Subsequently, the clear dissolved material was further diluted 1:10 using one of the above buffers. The outcome is shown in the following Table:

TABLE 12

|  | Tris* | TAPS** | Bicine*** | GlyGly**** |
|---|---|---|---|---|
| Resulting concentration of HCL | 1 mM | 1 mM | 1 mM | 1 mM |
| pH after addition of 1:10$^{th}$ acidic insulin | 8.89 | 8.94 | 9.0 | 8.91 |
| Precipitation in HIA1 and in-process batch step samples | + | + | − | + |

*Tris(hydroxymethyl) aminomethane, pKa = 8.3
**(N-tris[Hydroxymethyl]-3-aminopropanesulfonic acid, pKa = 8.4
***(N,N-bis[2-Hydroxyethyl)glycine), pKa = 8.3
****Glycylglycine, pKa = 8.2

In all examples the pH is unaltered or only minimally influenced after the addition of the acidic insulin solution. However, to our surprise only in Bicine buffer could a clear solution of HIA1 or in-process batch step samples be obtained consistently.

Therefore, choosing the Bicine buffer system represented a major break through in establishing a simple sample dissolution procedure and in obtaining stable analyte/buffer conditions during the incubation period of the immunoassay.

The invention claimed is:

1. A process for detecting or determining a C-peptide containing impurity comprising human C-peptide, monkey C-peptide, or a mixture thereof, in a sample of recombinantly produced human insulin or a derivative thereof, by a non-radioactive assay, comprising the steps of:
   (a) adding a C-peptide tracer to the sample;
   (b) adding antibody specific for the C-peptide containing impurity to the sample, said antibody being capable of recognizing human C-peptide and monkey C-peptide;
   (c) adding a C-peptide second antibody bead capable of capturing said antibody specific for the C-peptide containing impurity to the sample; and
   (d) detecting or determining the presence of the C-peptide-containing impurity in the sample,
   wherein the process is performed at a pH of about 8.5 to about 9.0.

2. The process according to claim 1, wherein the C-peptide-containing impurity is C-peptide, preproinsulin or a derivative thereof, or a C-peptide containing insulin or a derivative thereof.

3. The process according to claim 1, wherein the antibody specific for the C-peptide impurity additionally recognizes at least one compound selected from the group consisting of preproinsulin, reduced human insulin, alkylated human insulin, human insulin cleaved with endoproteinase, Lys (B3)-Glu(B29)-human insulin C-peptide, and Lys(B3)-Glu (B29)-human insulin preproinsulin.

4. The process according to claim 1, wherein the antibody specific for the C-peptide impurity recognizes both C-peptide and preproinsulin with nearly the same affinity.

5. The process according to claim 1, wherein the tracer is chemiluminescent.

6. The process according to claim 5, wherein the tracer comprises an acridinium ester moiety.

7. The process according to claim 1, wherein the presence of about 1 mg/mL human insulin does not interfere with the binding of the antibody specific for the C-peptide impurity.

8. The process according to claim 1, wherein the antibody specific for the C-peptide impurity is obtained by immunizing a mammal with a purified insulin C-peptide.

9. The process according to claim 8, wherein the mammal is a sheep.

10. The process according to claim 8, wherein the purified insulin C-peptide is monkey C-peptide.

11. The process according to claim 8, wherein the purified insulin C-peptide is human C-peptide.

12. A process for detecting or determining a C-peptide-containing impurity comprising human C-peptide, monkey C-peptide, or a mixture thereof, in a sample of recombinantly produced human insulin or a derivative thereof, by a non-radioactive assay, comprising the steps of:
   (a) adding a C-peptide tracer to the sample;
   (b) adding antibody specific for the C-peptide containing impurity to the sample, said antibody being capable of recognizing human C-peptide and monkey C-peptide;
   (c) adding a C-peptide second antibody bead capable of capturing said antibody specific for the C-peptide containing impurity to the sample; and
   (d) detecting or determining the presence of the C-peptide-containing impurity in the sample,
   wherein:
   (i) the presence of about 1 mg/ml human insulin does not interfere with the binding of the antibody specific for the C-peptide impurity; and
   (ii) the process is performed at a pH of 8.5 to about 9.0.

* * * * *